United States Patent [19]

Vaillancourt

[11] Patent Number: 5,147,314
[45] Date of Patent: Sep. 15, 1992

[54] APPARATUS FOR INTRODUCING AT LEAST ONE OF A CATHETER AND A GUIDE WIRE INTO A BODY CAVITY

[76] Inventor: Vincent L. Vaillancourt, 14 Bunyan Dr., Livingston, N.J. 07039

[21] Appl. No.: 793,861

[22] Filed: Nov. 18, 1991

[51] Int. Cl.⁵ .............................................. A61M 5/178
[52] U.S. Cl. .................................. 604/158; 604/163; 604/171
[58] Field of Search ............... 604/158, 161, 163, 167, 604/169, 206, 264, 905, 272, 171

[56] References Cited

U.S. PATENT DOCUMENTS

| | | | |
|---|---|---|---|
| 3,055,361 | 9/1962 | Ballard | 604/163 |
| 3,585,996 | 6/1971 | Reynolds et al. | 604/158 |
| 3,786,810 | 1/1974 | Pannier et al. | 604/158 |
| 4,235,232 | 11/1980 | Spaven et al. | 604/171 |
| 4,813,938 | 3/1989 | Raulerson | 604/167 |
| 4,842,591 | 6/1989 | Luther | 604/167 |
| 4,935,010 | 6/1990 | Cox et al. | 604/167 |
| 4,960,412 | 10/1990 | Fink | 604/167 |
| 5,041,097 | 8/1991 | Johnson | 604/264 |
| 5,062,836 | 11/1991 | Wendell | 604/167 |

*Primary Examiner*—Paul J. Hirsch
*Assistant Examiner*—Michael Lynch
*Attorney, Agent, or Firm*—Francis C. Hand

[57] ABSTRACT

A sheath which contains a catheter or guide wire is provided with a connector at one end which, in turn, has a sealing membrane which can be pierced by a hollow needle when the catheter/guide wire is to be expelled from the adaptor assembly. An introducer, which is to be implanted in a body cavity such as a blood vessel, also has a hub with a sealing membrane disposed across the hub so as to abut the sealing membrane of the adaptor assembly. This membrane is also pierced by the hollow needle when the connection is made prior to insertion of a catheter or guide wire into the blood vessel. In one embodiment, a syringe may be provided with a connector and mounted on the hub of the introducer.

8 Claims, 1 Drawing Sheet

APPARATUS FOR INTRODUCING AT LEAST ONE OF A CATHETER AND A GUIDE WIRE INTO A BODY CAVITY

This invention relates an apparatus for introducing at least one of a catheter and a guide wire into a body cavity.

As is known, various types of techniques have been used for the introduction of a catheter or a guide wire into a body cavity, such as a blood vessel, a spinal column and the like. For example, U.S. Pat. No. 4,813,938 describes the use of a syringe for the introduction of a catheter or guide wire into a blood vessel. As described, the syringe is of generally conventional structure having a barrel and a plunger slidably mounted within the barrel. In addition, the plunger is constructed with an internally disposed valve assembly through which a catheter or guide wire may be passed for introduction into a blood vessel. Generally, prior to threading, the syringe would be connected to an introducer in order to access the designated blood vessel. After aspiration, a guide wire can be threaded through the syringe and the valve assembly into the blood vessel. Thereafter, the syringe and the introducer can be withdrawn and discarded leaving the guide wire in place for further manipulation.

Although the syringe and an attached introducer may be considered a closed system, the threading of the guide wire or catheter is not since both the guide wire and a catheter are exposed to the environment during placement. Consequently, since the guide wire and/or catheter enters the body cavity any potential contamination is immediately transported into the patient.

Accordingly, it is an object of the invention to place a catheter or guide wire in a body cavity under closed system conditions.

It is another object of the invention to reduce the risk of contamination of a patient during the introduction of a guide wire or catheter.

Briefly, the invention provides an apparatus for introducing at least one of a catheter and a guide wire into a body cavity in a sterile manner.

The apparatus includes an introducer having a tubular portion for introduction into a body cavity, a hub at a proximal end of the tubular portion and a sealing membrane disposed at a proximal end of the hub in sealed relation.

The apparatus also includes an adaptor assembly having a connector at one end with a tubular housing for slidably receiving the hub of the introducer, a collapsible tube concentrically within the housing and a sealing membrane at a distal end of the tube. In addition, the adaptor assembly has a hollow needle for forming a passage through the sealing membrane when the tube is collapsed about the needle. The adaptor assembly also has a flexible sheath mounted on the tubular housing in seal-tight relation and extending from the housing, a closure at a proximal end of the sheath and a catheter or guide wire extending within the sheath in spaced relation to the sealing membrane in the connector.

In this embodiment, in order to place the catheter or guide wire in the body cavity, the connector of the adaptor assembly is secured to and over the hub of the introducer. At this time, the introducer moves into the connector causing a collapse of the collapsible tube and piercing of the hollow needle through the sealing membrane. Thereafter, the catheter or guide wire can be moved through the hollow needle and the introducer. During this time, the catheter or guide wire is retained in a sterile condition in a closed system.

In another embodiment, a syringe may be used in combination with the introducer and the connector. In this respect, the syringe is provided with a barrel, a hollow tip extending from the barrel and a plunger slidably mounted in the barrel. In addition, the connector is provided with a tubular housing which is mounted on and which extends from the tip of the syringe for slidably receiving the hub of the introducer therein. The connector is constructed as above with a hollow needle in line with the tip of the syringe, a collapsible tube disposed about the tip of the syringe and a sealing membrane across the tube in sealed relation and in spaced relation to the hollow needle.

In this embodiment, the contents of the syringe may be retained in a sterile condition being sealed at opposite ends by the plunger of the syringe and the sealing membrane of the connector.

In still another embodiment, the introducer may have a Y-site connector extending from the tubular portion with a pair of arms. One arm is sized to receive a syringe while the second arm is provided with a piercable sealing membrane for coaction with a wire guide adaptor assembly. In this embodiment, with a syringe still in place, the connector of the guide wire adaptor assembly may be connected to the side arm so that the guide wire can be threaded into the blood vessel under closed system conditions.

These and other objects and advantages of the invention will become more apparent from the following detailed description taken in conjunction with the accompanying drawings wherein.

Figure 1:
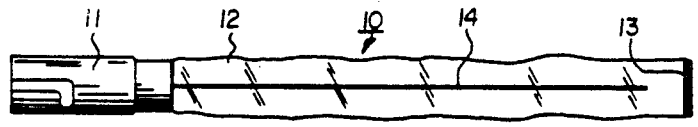
FIG. 1 illustrates a view of an adaptor assembly constructed in accordance with the invention.

Referring to FIG. 1, the apparatus for introducing a catheter or guide wire into a blood vessel is provided with an adaptor assembly 10 having a connector 11 at one end, a flexible sheath 12 secured to the connector 11 in seal-tight relation and a closure 13 at a proximal end of the sheath 12. This closure 13 may be in the form of a hub which is slidably mounted on a catheter 14 or, where a guide wire is disposed within the sheath 12, the closure 13 may be releasably secured to the proximal end of the guide wire in a manner not shown. In this respect, as the guide wire would normally be left in place in a blood vessel or other body cavity, the closure 13 is not permanently secured to the guide wire so as to permit a subsequent separation therefrom.

Figure 6:
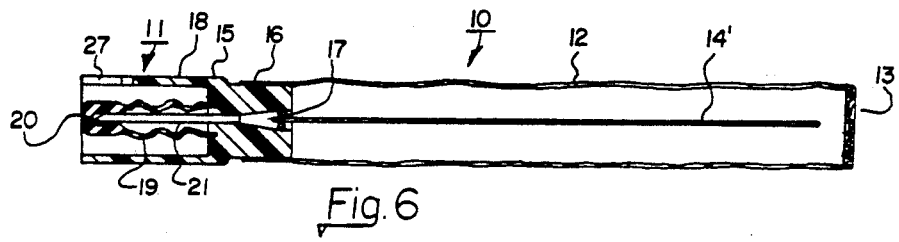
FIG. 6 illustrates a cross-sectional view of the guide wire adaptor of FIG. 2.

Referring to FIG. 6, the connector 11 is constructed in a manner as described in pending U.S. patent application Ser. No. 07/647,782, filed Jan. 30, 1991, for example, with a hub 15 from which a stub portion 16 extends proximally for receiving the sheath 12 in sealed relation thereon. In addition, the extension 16 has a seal ring 17, such as an 0-ring having the catheter 14' slidably received therein in seal-fit relation. This seal 17 serves to prevent both the egress of blood or spinal fluid and the ingress of potentially threatening air.

The connector 11 also has a tubular portion 18 extending from the hub 15 and a collapsible tube 19 secured at one end to the hub 15. A sealing membrane 20 is secured to the distal end of the collapsible tube 19 to seal off the interior of the sheath 12. As indicated, the sealing membrane 20 is spaced from the distal end of the catheter 14.

The connector 11 also has a hollow needle 21 mounted in the hub 15 which is aligned with the catheter 14 and which has a blunt or sharp end facing or received in a bore of the sealing membrane 20.

Figure 2:
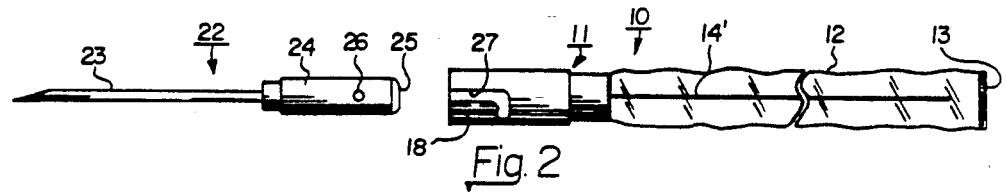
FIG. 2 illustrates an exploded view of an introducer and guide wire adaptor assembly constructed in accordance with the invention.

Referring to FIG. 2, the apparatus also includes an introducer 22 having a tubular portion 23 for piercing through the skin of a patient for introduction into a blood vessel (not shown). The introducer 22 also has a hub 24 at a proximal end and a sealing membrane 25 disposed at a proximal end of the hub 24 in sealed relation. As illustrated, the hub 24 is of a size so as to slidably fit within the tubular housing 18 of the connector 11. A suitable means is also provided for securing the hub 24 to the connector 11. For example, the hub 24 is provided with a pair of pins 26 (only one of which is shown) while the tubular housing 18 of the hub 24 is provided with a pair of L-shaped slots 27 (only one of which is show). Coupling of the hub 24 with the connector 11 is effected by sliding of the pins 26 into the slots 27 with a slight subsequent rotation of the connector 11 to hold the pins 26 in place.

In use, after the introducer 22 has been inserted into a blood vessel or other body cavity using known techniques, an adaptor assembly 10 containing a guide wire 14' is secured to the hub 24. To this end, the connector 11 is slid over the hub 24 with the sealing membranes 20, 25 abutting each other in seal tight fashion. At this time, the collapsible tube 19 collapses and the hollow needle 21 pierces both sealing membranes 20, 25. After connection has been made, the wire guide 14' which is mounted in the sheath 12 as in FIG. 6 can be slid through the hollow needle 21 into the blood vessel. The wire guide 14' may also extend into the hollow needle (cannula) 21 to just before the sharp end.

The wire guide 14' can be left in place while the remainder of the adaptor assembly 10 and the introducer 20 are subsequently withdrawn.

Where the adaptor assembly 10 contains a catheter 14, the catheter 14 is mounted in the same way as a guide wire and may be slid through the hollow needle 21. The catheter 14 does not extend beyond the sheath 12 but is totally contained within the sheath 12 as shown. In this case, the guide wire/catheter is manipulated forward out of the sheath 12 and into the vessel through external finger manipulation through the sheath 12.

Figure 3:
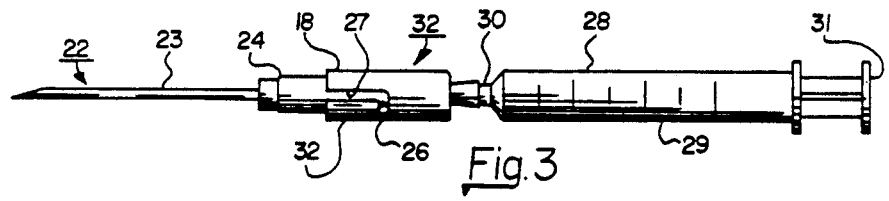
FIG. 3 illustrates a view of an introducer and a syringe constructed in accordance with the invention.

Referring to FIG. 3, wherein like reference characters indicate like parts as above, instead of using an adaptor assembly container a catheter or guide wire, use may be made of a syringe for the introduction of a catheter or guide wire. To this end, the syringe 28 has a barrel 29 of conventional structure, a hollow tip 30 extending from the barrel 29 and a plunger 31 slidably mounted within the barrel 29. In addition, a connector 32 is mounted on the tip 30 of the syringe 28. This connector 32 is constructed in similar manner as above described so as to have a tubular portion 18 slidably received over the hub 24 of the introducer 22 while being fitted over the tip 30 of the syringe 28.

In this embodiment, there is no need for an extension on the connector 11 as in the embodiment illustrated in FIG. 6.

When in use, the syringe 28 is provided with the connector 32 so as to seal the contents of the barrel 29. The connector 32 can then be connected to the hub 22 of the introducer 22 when a catheter or guide wire is to be introduced into the introducer 22.

Figure 4:
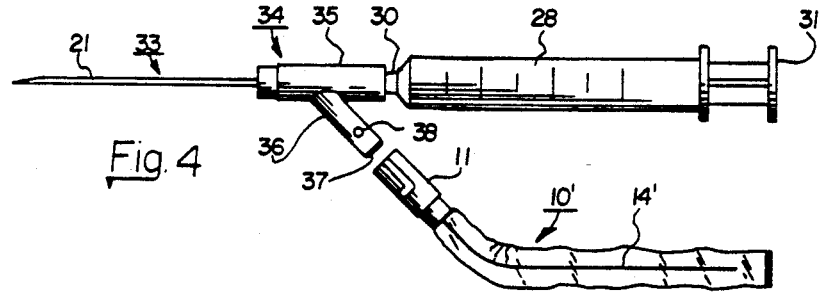
FIG. 4 illustrates a view of an introducer having a Y-site connector in combination with a syringe and a guide wire adaptor assembly in accordance with the invention.
Figure 5:
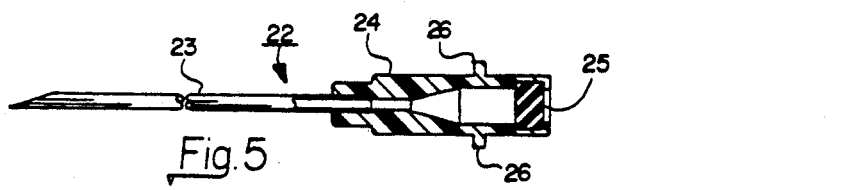
FIG. 5 illustrates a cross sectional view of the introducer of FIG. 2.

Referring to FIG. 4, an introducer 33 may be provided with a Y-site connector 34 at a proximal end of a tubular portion 21. As indicated, this Y-site connector 34 has a first arm or hub 35 for permanently receiving the hollow tip 30 of the syringe 28. In addition, the Y-site connector 34 has a second arm 36 of conventional structure provided with a piercable sealing membrane 37 at the free end as well as with pins 38 for releasable connection to an adaptor assembly 10 as described above. For example, in this case, the adaptor assembly 10 has a guide wire 14' therein to be threaded through the Y-site connector 34 into the introducer tubular portion 21 for implanting in a blood vessel (not shown).

In use, the syringe 28 is connected to the introducer 33 via the connector 34 and is used to aspirate fluid and aid in determining that the vessel has been penetrated. Thereafter, o puncture of the designated blood vessel Or other body cavity is effected. After a flashback of blood or other body fluid has been obtained, the syringe 28 can be removed and the guide wire/catheter assembly 10 can be attached to the introducer 22. Next, the guide wire/catheter 14, 14' is threaded through the sheath 12 and into the blood vessel while remaining under a closed system.

The invention thus provides an apparatus which permits the introduction of a catheter and/or guide wire into a body cavity, such as a blood vessel, in a sterile manner.

Further, the invention provides an apparatus which is able to maintain a catheter or guide wire in a sealed sterile condition at all times.

What is claimed is:

1. An apparatus for introducing at least one of a catheter and a guide wire into a body cavity, said apparatus comprising an introducer having a tubular portion for introduction into a body cavity, a hub at a proximal end of said tubular portion and a first membrane disposed at a proximal end of said hub in sealed relation;

a syringe having a barrel, a hollow tip extending from said barrel and a plunger slidably mounted in said barrel; and a connector having a tubular housing mounted on and extending from said tip of said syringe for slidably receiving said hub of said introducer therein, a collapsible tube disposed about said tip and a second membrane disposed across said tube in sealed relation and in spaced relation to said tip to abut said first membrane in seal-tight relation.

2. An apparatus as set forth in claim 1 which further comprises a catheter assembly having a second connector at one end with a tubular housing for slidably receiving said hub of said introducer therein, a second collapsible tube concentrically within said housing, a second membrane at a distal end of said tube and a hollow needle in alignment with said second membrane for passage through said second membrane in response to collapsing of said tube; a flexible sheath mounted on said tubular housing in seal-tight relation and extending from said housing; a closure at a proximal end of a said sheath and a catheter extending from said closure and within said sheath in alignment with said hollow needle.

3. An apparatus as set forth in claim 1 which further comprises a guide wire assembly having a connector at one end with a tubular housing for slidably receiving said hub of said introducer therein, a collapsible tube concentrically within said housing, said second membrane at a distal end of said tube and a hollow cannula in alignment with said second membrane for passage through said second membrane in response to collapsing of said tube; a flexible sheath mounted on said tubular housing in seal-tight relation and extending from said housing; a closure at a proximal end of a said sheath and a guide wire extending within said sheath in alignment with said hollow cannula.

4. An apparatus as set forth in claim 1 which further comprises means for securing said hub of said introducer with said connector.

5. An apparatus for introducing a catheter into a body cavity, said apparatus comprising an introducer having a tubular portion for introduction into a body cavity, a hub at a proximal end of said tubular portion and a first membrane disposed at a proximal end of said hub in sealed relation; and an adapter assembly having a connector at one end with a tubular housing slidably receiving said hub of said introducer therein, a collapsible tube concentrically within said housing, a second membrane at a distal end of said tube for abutting said first membrane and a hollow cannula fixedly mounted in said housing within said tube in alignment with said second membrane for passage through said second membrane in response to collapsing of said tube; a flexible sheath mounted on said tubular housing in seal-tight relation and extending from said housing; a closure at a proximal end of a said sheath and a catheter extending from said closure and within said sheath in alignment with said hollow needle.

6. An apparatus as set forth in claim 5 which further comprises means for releasably securing said hub to said connector.

7. An apparatus as set forth in claim 5 wherein said sheath is transparent.

8. An apparatus for introducing a guide wire into a blood vessel, said apparatus comprising an introducer having a tubular portion for introduction into a body cavity, a Y-site connector extending from said tubular portion and having a first arm and a second arm, and a first penetrable membrane disposed across said second arm;

a syringe having a barrel, a hollow tip extending from said barrel into said first arm, and a plunger slidably mounted in said barrel; and a wire guide assembly having a connector at one end with a tubular housing slidably receiving said second arm or said Y-site connector therein, a collapsible tube concentrically within said housing, a second membrane at a distal end of said tube and a hollow needle in said housing and within said tube for passing through said membranes in response to insertion of said second arm in said housing; a flexible sheath mounted on said tubular housing in seal-tight relation and extending from said housing; a closure at a proximal end of said sheath and a wire guide extending within said sheath in alignment with said hollow cannula.

* * * * *

UNITED STATES PATENT AND TRADEMARK OFFICE
CERTIFICATE OF CORRECTION

PATENT NO. : 5,147,314

DATED : September 15, 1992

INVENTOR(S) : VINCENT L. VAILLANCOURT

It is certified that error appears in the above-identified patent and that said Letters Patent is hereby corrected as shown below:

```
Column 4, line 21 cancel "o"
  Line 30 change "Or" to -or-
Column 6, line 25 change "or" to -of-
```

Signed and Sealed this

Seventh Day of September, 1993

Attest:

BRUCE LEHMAN

*Attesting Officer*     *Commissioner of Patents and Trademarks*